United States Patent [19]
Robinson

[11] Patent Number: 4,955,913
[45] Date of Patent: Sep. 11, 1990

[54] SURGICAL TIE

[76] Inventor: Walter C. Robinson, 109 E. Kenilworth Dr., Greenville, S.C. 29615

[21] Appl. No.: 387,409

[22] Filed: Jul. 31, 1989

Related U.S. Application Data

[63] Continuation of Ser. No. 717,286, Mar. 28, 1985, abandoned.

[51] Int. Cl.⁵ .............................................. A61L 17/00
[52] U.S. Cl. ...................................... 606/228; 606/232
[58] Field of Search ................ 128/335, 335.5, 334 R, 128/325, 326, 327; 528/354; 24/16 PB; 606/228, 229, 230, 231, 232

[56] References Cited

U.S. PATENT DOCUMENTS

| 2,756,753 | 7/1956 | Means | 128/325 X |
|---|---|---|---|
| 3,331,814 | 7/1967 | Randall | 128/335.5 |
| 3,537,146 | 11/1970 | Caveney | 24/16 PB |
| 3,570,497 | 3/1971 | Lemole | 24/16 PB X |
| 3,985,138 | 10/1976 | Jarvik | 128/335.5 X |
| 4,033,938 | 7/1977 | Augurt et al. | 528/354 |
| 4,052,988 | 10/1977 | Doddi et al. | 128/335.5 |
| 4,441,496 | 4/1984 | Shalaby et.al. | 128/335.5 |
| 4,559,945 | 12/1985 | Koelmel et al. | 528/354 X |

FOREIGN PATENT DOCUMENTS 2102827  2/1983  United Kingdom ................ 528/354

OTHER PUBLICATIONS

A Simplified Method for Closure of the Chest Wall, by William E. Neville, M.D., and Roque Pifarre, M.D., reprinted from The Annals of Thoracic Surgery, vol. 7, No. 1, Jan. 1969, pp. 44–46.

Primary Examiner—Henry A. Bennet
Attorney, Agent, or Firm—Bailey & Hardaway

[57] ABSTRACT

An absorbable surgical tie which permits positive locking an quick adaptation, particularly during the performance of feline and canine hysterectomies.

4 Claims, 2 Drawing Sheets

SURGICAL TIE

This application is a continuation of application Ser. No. 717,286, filed 3/28/85, now abandoned.

BACKGROUND OF THE INVENTION

This invention relates generally to the art of surgery and more particularly to a tieing device for utilization during surgery.

Various sutures and tieing devices have been developed heretofore in the prior art. Various sutures have been prepared from special materials which permit their absorption or dissolution into the living organism into which they are utilized.

Additionally there have been utilized tieing devices for ligating various tissues.

SUMMARY OF THE INVENTION

It is thus an object of this invention to provide a novel surgical tie;

It is a further and more particular object of this invention to provide an absorbable surgical tie which permits positive locking and quick adaptation, particularly during the performance of feline and canine hysterectomies.

These as well as other objects are accomplished with a surgical tie comprising an elongated strap having a retaining head at one end and a tongue portion at the other end. The retaining head has a strap receiving end locking means for receiving and positively retaining the tongue portion against movement in one direction so as to form a surgical tie into a loop around living tissue and ligate such tissue. The surgical tie is formed of a polymer composition of dioxannone which is absorbable into living tissue.

DETAILED DESCRIPTION

Figure 1:
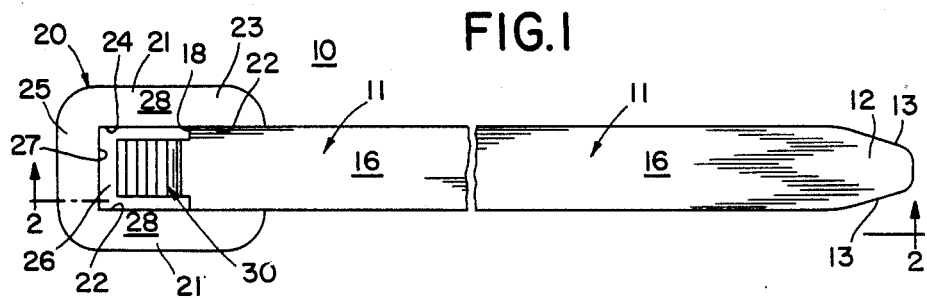
FIG. 1 is a plan view of an integral one-piece surgical tie made in accordance with and embodying the principles of the present invention.
Figure 2:
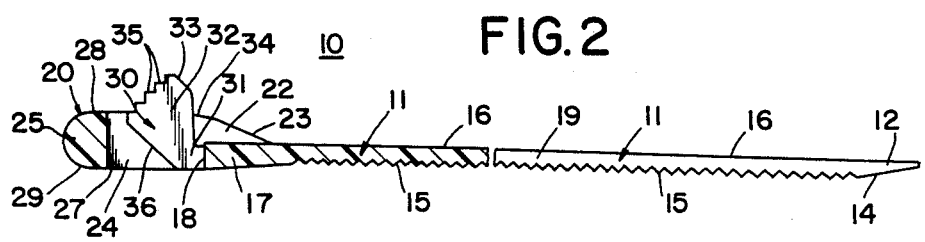
FIG. 2 is a side view with certain portions in section of the surgical tie of FIG. 1 substantially as viewed in the direction of the arrows along the line 2—2 thereof.

Referring to the drawings, and particularly to FIGS. 1 and 2 thereof, there is shown an integral one-piece surgical tie 10 made in accordance with and embodying the principles of the present invention. The surgical tie 10 includes generally a strap 11 carrying on one end thereof a frame or head 20 having a strap-receiving opening 26 therethrough in which is positioned a pawl 30.

The surgical tie 11 is elongated and flexible and includes an outer end 12 which is provided with tapered sides 13 as well as an inclined surface 14 on the lower side thereof as viewed in FIG. 2, whereby the outer end 12 has reduced dimensions in both the transverse direction and in the thickness thereof. The underside of the tie 11 as illustrated in FIG. 2 is provided with an essentially continuous row of engagement members or teeth 15. The teeth 15 as illustrated extend from and adjacent to the outer end 12 to a point adjacent to the frame 20. The other surface 16 of the tie 11 is formed smooth and essentially flat as molded. The end of the tie 11 opposite the outer end 12 has a thickened section 17 that terminates in an end wall 18 that is disposed essentially normal to the longitudinal axis of the tie 11 as molded. The tie 11 further is provided with a pair of essentially parallel tie sides 19 that extend the length thereof, i.e., from adjacent to the outer end 12 to the thickened section 17.

The frame 20 is integral with the tie 11 and comprises the thickened section 17, a pair of side members 21 and an end member 25. The side members 21 are integral with the tie 11 at the thickened section 17 and extended from the lower surface thereof upwardly above the smooth surface 16 of the tie 11 as illustrated in FIGS. 2 and 4 to 7. More specifically, the side members 21 are respectively provided with inner surfaces 22 that are disposed essentially parallel to each other and are disposed in the same planes as the strap sides 19. The upper sides of the side members 21 are provided with upwardly inclined surfaces 23, as viewed in FIG. 2, whereby the main portion of the side members 21 have a thickness that is substantially greater than the thickness of the tie 11 and even the thickness of the thickened section 17 of the tie 11. The inner surfaces 22 merge into side walls 24 provided on the inwardly facing portions of the side members 21 adjacent to the juncture thereof with the end member 25. The end member 25 is provided with an end wall 27, spaced from the end wall 18 and disposed essentially parallel thereto. The end walls 18 and 27 are also perpendicular respectively to the side walls 24, the end walls 18 and 27 and the side walls 24 defining therebetween the strap-receiving opening 26 in the frame 20. The upper surfaces of the side members 21 and the end member 25 lie in a common plane and define a common upper or exit surface 28, and the lower surface of the side members 21 and the end member 25 lie in a common plane and define a common lower or entry surface 29. The lower surface 29 is formed essentially as a continuation of the lower side of the tie 11 as molded and as viewed in FIG. 2, but the upper surface 28 is disposed well above the strap surface 16 since the frame 20 has a thickness substantially greater than that of the tie 11. It also will be noted that the outer edges of the frame 20 including the outer edges of the side members 21 and the end members 25 are rounded, whereby there are no sharp corners or edges on which items would be accidentally torn or cut during use of the surgical tie 10.

Figure 5:
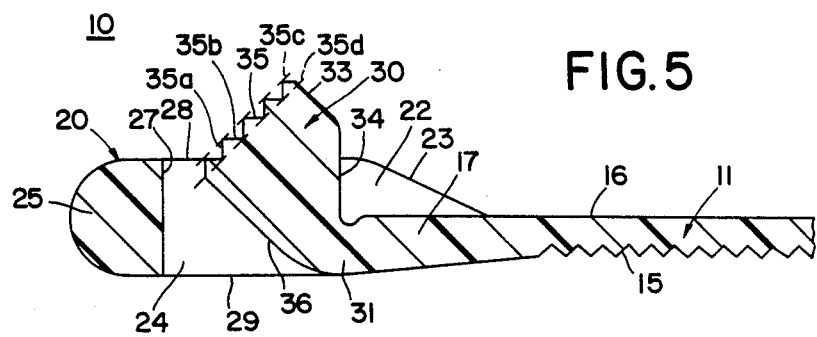
FIG. 5 is a view in vertical section along the line 5—5 of FIG. 4.
Figure 6:
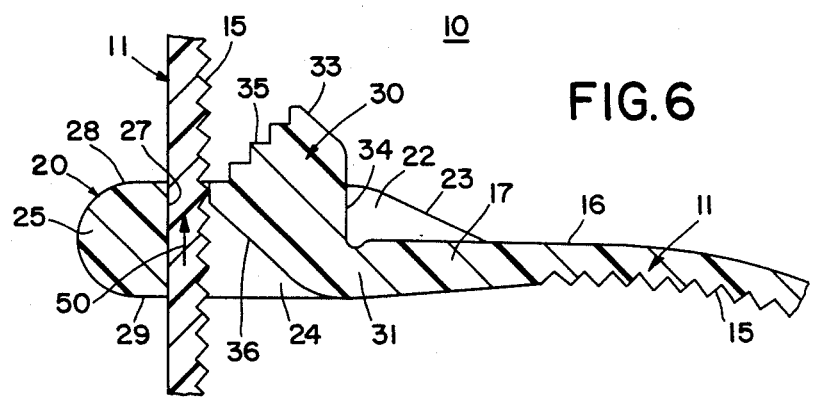
FIG. 6 is a view similar to FIG. 5 showing the parts in the positions assumed during insertion of the strap end of the surgical tie through the frame and past the pawl therein.
Figure 7:
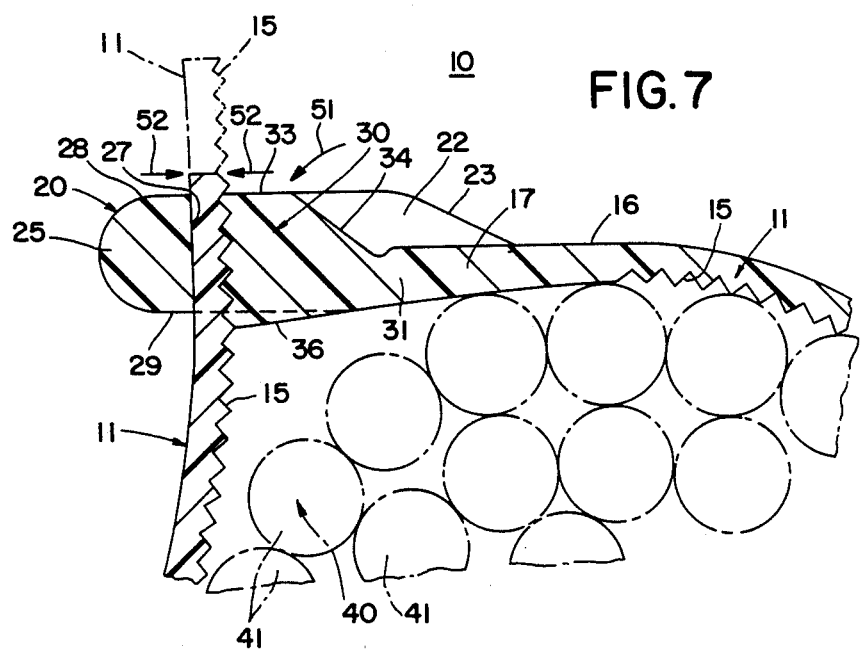
FIG. 7 is a view similar to FIG. 5 showing the parts of the surgical tie in the locking positions thereof.

The pawl 30 is hingedly mounted on and integral with the frame 20, and specifically is integral with the thickened section 17. As best seen in FIGS. 5 to 7, there is a narrow neck joining the pawl 30 and the thickened section 17 to provide a hinge section 31 that is well defined, thus to facilitate hinged movement of the pawl 30 with respect to the frame 20, and specifically with respect to the thickened section 17 thereof. Referring to FIG. 1, it will be seen that the width of the pawl 30 is substantially less than the width of the tie 11 and the width of the tie-receiving opening 26; the pawl 30 is further provided with a pair of parallel side surfaces 32 that are disposed essentially normal to the end wall 18 and the end wall 27 and that are disposed essentially parallel to the side walls 24. The pawl 30 is essentially wedge shaped in side view as seen in FIG. 2 and has a top surface 33 that joins with an inclined surface 34 that joins the top surface 33 and the hinge section 31. The surface of the pawl 30 disposed toward the end wall 27 is a strap-engaging surface and carried thereon a set of teeth 35 that are shaped complementary to the row of teeth 15 formed on the tie 11, each of the teeth 35 having a first surface 35a disposed essentially vertically as illustrated in FIGS. 5 and 6 and disposed toward the lower or entry surface 29 in the tensioned condition of FIG. 7 and each of the teeth 35 having a second surface 35b disposed essentially horizontally as illustrated in FIGS. 5 and 6 and disposed toward the upper or exit surface 38 in the tensioned condition of FIG. 7; the crests of the teeth 35 lie in a common plane diagrammatically illustrated in FIG. 5 by the dashed lines 35c and the roots of the teeth 35 likewise lie in a common plane diagrammatically illustrated by the dashed line 35d in FIG. 5. The surface of the pawl 30 on which the teeth 35 are formed is disposed essentially normal to the top surface 33 and extends downwardly to a lower surface 36 which joins the teeth 35 to the hinge section 31. The end wall 27 on the end member 25 provides a strap-bearing surface, as will be described more fully hereinafter, and the end wall 27 and the wall of the pawl 30 carrying the teeth 35 define therebetween a strap-receiving channel disposed within the strap-receiving opening 26 in the frame 20.

The surgical tie 10 is shown in the as-molded condition in FIGS. 1 and 2, wherein it will be seen that the tie 11 is essentially straight and the pawl 30 is biased and positioned upwardly with respect to the frame 20 and extends well above the upper surface 28 thereof with the inclined surface 34 disposed almost normal to the tie surface 16 and with thesurface carrying the set of teeth 35 disposed at an angle of approximately 45 degrees with respect to the strap surface 16 and the end wall 27.

Figure 3:
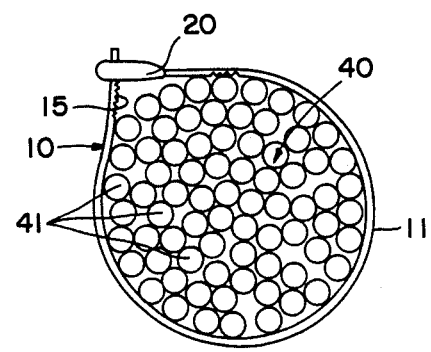
FIG. 3 is a diagrammatic view illustrating the surgical tie of FIG. 1 applied to a bundle of wires.
Figure 4:
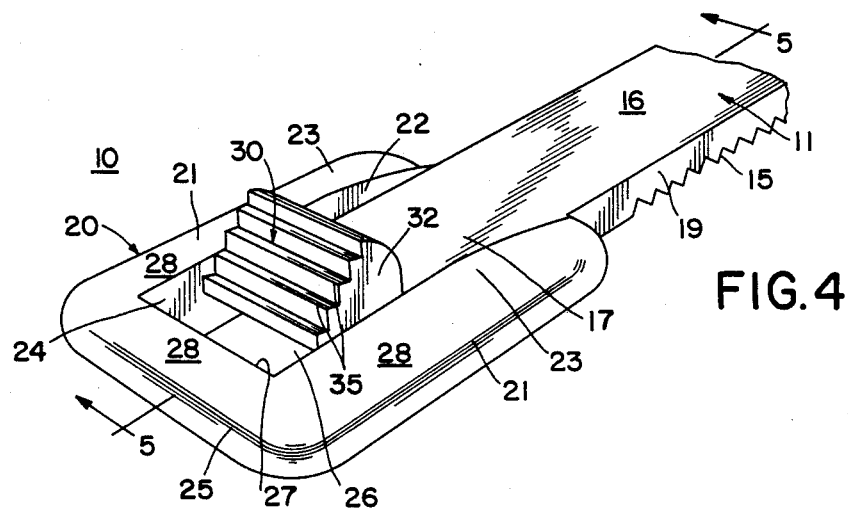
FIG. 4 is an enlarged fragmentary perspective view of the end of the surgical tie including the head and the pawl forming a part thereof.

The tie 11 is deformable into a loop for encircling the bundle 40 of the tissue 41, it being noted that the row of teeth 15 is disposed inwardly and against the bundle 40, see FIG. 3. The outer end 12 is first inserted into the tie-receiving opening 26 and is guided by the lower surface 36 on the pawl 30 into the tie-receiving channel between the end wall 27 and the pawl 30. Eventually the teeth 15 will come into contact with the pawl 30 at which time it may be necessary that the pawl 30 be pivoted in a clockwise direction as viewed in FIGS. 2, 5 and 6, which pivotal movement is accommodated by the fact that there is no obstruction in the path of the inclined surface 34, i.e., the inner surfaces 22 are spaced apart a distance greater than the width of the pawl 30, whereby the pawl 30 may be freely pivoted in a clockwise direction to a substantial degree. Movement of the tie 11 through the head 20 and past the pawl 30 is in the direction of the arrow 50 in FIG. 6 during the tightening of the tie 11 about the bundle 40. Once the tie 11 extends beyond the head 20, and specifically beyond the upper surface 28 as a result of manual manipulation of the surgical tie 20, that portion of the tie 11 about the surface 28 in FIG. 6 can be grasped to tighten the surgical tie 10 about the bundle 40 by pulling the tie 11 in the direction of the arrow 50 in FIG. 6. After the desired degree of tension has been placed in the tie 11, that portion of the tie 11 above the frame 20 in FIG. 6 is released, whereby the resiliency in the tie 11 and the tension exerted by the bundle 40 will move the tie 11 downwardly with respect to the head 20 as viewed in FIG. 7, thereby to cause engagement between the set of teeth 35 on the pawl 30 and certain ones of the teeth 15. Such movement of the tie 11 with respect to the head 20 pivots the pawl 30 in a counterclockwise direction, and in the direction of the arrow 51 in FIG. 7, so as to place the parts in the position of FIG. 7. With the parts in the positions illustrated in FIG. 7, the pawl 30 clamps the tie 11 against the end wall 27, thus firmly to hold the tie 11 and to prevent further movement thereof downwardly with respect to the frame 20 as viewed in FIG. 7. For convenience sake, the portion of the tie 11 disposed above the frame 20 may then be cut as diagrammatically illustrated by the arrows 52 in FIG. 7, and the portion of the tie 11 disposed thereabove and illustrated by dashed lines may be discarded.

From FIG. 7, it will be seen that a plurality of the teeth 35 are disposed opposite the end wall 27, whereby the portion of the tie 11 disposed therebetween is backed up by the end wall 27. As illustrated, four of the teeth 35 on the pawl 30 are thus disposed opposite the end wall 27, whereby it will be appreciated that the three full teeth 35 disposed within the strap-receiving opening 24 actually have the end wall 27 extending upwardly and downwardly with respect thereto, whereby these three engaged teeth are encompassed thereby. All of the teeth 35 in the tensioned condition are engaged and loaded, the teeth have sequentially engaged successive ones of the teeth 15 during the tensioning operation. The above described tensioning operation is made possible due to the fact that the pawl 30 terminates at points spaced from the end wall 27 in all positions of the pawl 30, i.e., a distance is preserved between the pawl 30 and the end wall 27 that is less than or no greater than the thickness of the tie 11 in all positions of the pawl 30. In the tensioned condition of FIG. 7, no part of the pawl 30 extends beyond the exit surface 28 of the frame 20 and the portion of the tie 11 engaged between the pawl 30 and the end wall 27 has access thereof disposed parallel to the end wall 27 and normal to the entry surface 29, the end wall 27 being disposed to the entry surface 29.

The surgical tie 10 is now firmly secured about the bundle 40 and cannot be readily removed therefrom. In fact, any force tending to withdraw the tie 11 from within the frame 20 in a strap-loosening direction only serves to move the teeth 35 on the pawl 30 into more firm engagement with the engaged ones of the teeth 15 on the tie 11. In other words, the pawl 30 serves firmly to wedge the tie 11 into firm locking engagement with the end wall 27 to prevent withdrawal of the tie 11 from the frame 20. As a consequence, the surgical tie 20 is locked in its tensioned condition about the bundle 40.

It is pointed out that with the parts of the locked positions of FIG. 7, the top surface 33 of the pawl 30 is essentially flush with the upper surface 28 of the frame 20. The surface of the pawl 30 carrying the teeth 35 is disposed essentially parallel to the end wall 27. As a result, a neat and unobstructed configuration is provided at the juncture between the tie 11 and the head 20, all while maintaining a firm grip upon the engaged portion of the tie 11 within the frame 20.

Such apparatus is generally described in U.S. Pat. No. 3,537,146 which is herewith incorporated by reference.

The apparatus as described above is formed of a special polymer so as to be absorbable into living tissue. It is preferred to utilize the apparatus of this invention by encircling the apparatus about the living tissue to be ligated such as female reproductive organs in feline and canine animals. The strap is tightened to the point where there is insignificant fluid communication from one side of the tie to the other and then severing the unwanted portion. Thus by utilizing the surgical tie of this invention in a miniumum of steps the unwanted tissues are removed and the remaining living tissue is left in a secure arrangement which permits healing and the absorption of the composition of the surgical tie.

The surgical tie is preferably formed of a polydioxanone material of the types described in U.S. Pat. Nos. 4,052,988, 3,063,967, 3,636,956 and 3,297,033.

Polymers of the present invention are comprised of units having a general formula:

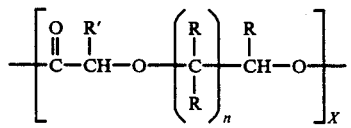

R' and R are individually hydrogen, methyl, or ethyl, n is 1 or 2 provided that when n is 2 at least two R groups are hydrogen, and X is the degree of polymerization resulting in a fiber forming polymer.

The polymer is conveniently prepared from highly purified monomer, i.e., monomer of at least about 98 mode percent having the formula:

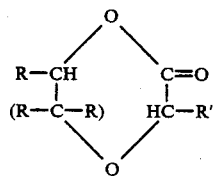

wherein R, R' and n are as defined above. When n is 1, the monomer is preferably p-dioxanone, methyl-p-dioxanone, or dimethyl-p-dioxanone. When n is 2, the monomer is preferably 1,4-dioxepan-2-one.

A particularly preferred monomer is p-dioxanone, and the following description and examples which are presented by way of illustration are directed primarily to the preparation and polymerization of that monomer, it being understood that certain variations may apply to other monomers and polymers encompassed by the above formula as will be readily apparent to those skilled in the art. Para-dioxanone monomer is conveniently prepared by reacting ethylene glycol, metallic sodium, and choloroacetic acid as hereinafter described in detail. The resulting monomer is preferably purified to 99+ % purity by multiple distillations and recrystallizations. A high monomer purity is necessary to obtain a high molecular weight polymer and ultimately, a fiber of good tensile and dry knot strength.

The purified monomer is polymerized at a temperature of 20 degrees to 130 degrees C., most preferably above 75 degrees C., in the presence of an organometallic catalyst as hereinafter described in detail to obtain a high molecular weight polymer of p-dioxanone characterized by an inherent viscosity of at least about 0.50 measured as a 0.1% solution in tetrachloroethane at 25 degrees C., and a crystallinity of at least about 20% as determined by X-ray diffraction.

The described surgical tie is designed for, but not limited to, ligations of vessels associated with the ovario hysterectomies of companion animals. This surgical tie can easily be placed around the entire cervix and drawn tight to establish excellent occlusion of the cervix and associated uterine vessels. Additionally, the tie is used to ligate the ovarian arteries in like manner.

It is thus seen that the surgical tie of this invention provides a novel surgical tie which is absorbable into living tissue. It additionally permits the quick and effective performance of feline and canine hysterectomies while leaving behind a ligature which is absorbable into living tissue. As many variations will become apparent to those of skill in the art from a reading of the above description, such variations are embodied within the spirit and scope of the following appended claims:

I claim:

1. A surgical tie for use as a ligature in surgical procedures comprising:

an elongated flexible strap;

a frame integral with one end of said strap, said frame including a pair of longitudinally extending and spaced-apart side walls and an end wall joining the outer ends of said side walls and having a strap-receiving opening therethrough;

a row of teeth disposed on one longitudinal surface of said strap and arranged transversely with respect thereto;

a pawl hingedly mounted on and integral with said frame and extending into said strap-receiving opening toward said end wall, said end wall having a strap-bearing surface disposed toward said pawl and said pawl having a strap-engaging surface disposed toward said end wall and defining therewith a strap-receiving channel;

a set of teeth disposed on said strap-engaging surface of said pawl and arranged transversely with respect thereto and shaped complementary to said row of teeth on said strap, said strap being deformable into a loop encircling a bundle of wires with the other end of said strap extending into said strap-receiving channel and through the opening in said frame and therebeyond, said set of teeth being disposed toward said row of teeth as said strap is tightened about living tissue to a tensioned condition, said set of teeth upon release of said tensioned strap sequentially moving into firm engagement with and remaining in firm engagement with successive adjacent ones of said row of teeth, any force tending to withdraw said strap from within said strap-receiving channel in a strap-loosening direction serving to move said set of teeth into more firm engagement with the engaged ones of said row of teeth firmly to wedge said strap between said strap-bearing surface and said strap-engaging surface so as to form said surgical tie into a loop around living tissues and ligate same;

said elongated strap formed of a polymer having a general formula:

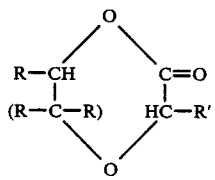

wherein R' and R are individually hydrogen, methyl or ethyl.

2. The surgical tie according to claim 1 wherein R and R' are hydrogen and the monomer is p-dioxanone.

3. A surgical tie for use as a ligature in surgical procedures comprising:

an elongated flexible strap;

a frame integral with one end of said strap, said frame including a pair of longitudinally extending and spaced-apart side walls and an end wall joining the outer ends of said side walls and having a strap-receiving opening therethrough;

a row of teeth disposed on one longitudinal surface of said strap and arranged transversely with respect thereto;

a pawl hingedly mounted on and integral with said frame and extending into said strap-receiving opening toward said end wall, said end wall having a strap-bearing surface disposed toward said pawl and said pawl having a strap-engaging surface disposed toward said end wall and defining therewith a strap-receiving channel;

a set of teeth disposed on said strap-engaging surface of said pawl and arranged transversely with respect thereto and shaped complementary to said row of teeth on said strap, said strap being deformable into a loop encircling a bundle of wires with the other end of said strap extending into said strap-receiving channel and through the opening in said frame and therebeyond, said set of teeth being disposed toward said row of teeth as said strap is tightened about living tissue to a tensioned condition, said set of teeth upon release of said tensioned strap sequentially moving into firm engagement with and remaining in firm engagement with successive adjacent ones of said row of teeth, any force tending to withdraw said strap from within said strap-receiving channel in a strap-loosening direction serving to move said set of teeth into more firm engagement with the engaged ones of said row of teeth firmly to wedge said strap between said strap-bearing surface and said strap-engaging surface so as to form said surgical tie into a loop around living tissues and ligate same;

said elongated strap formed of a polymer having a general formula:

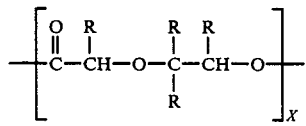

wherein R' and R and individually hydrogen, methyl, or ethyl and x is the degree of polymerization.

4. A process of ligating living tissue in vivo, comprising the steps of:

providing a surgical tie for use as a ligature in surgical procedures comprising:

an elongated flexible strap;

a frame integral with one end of said strap, said frame including a pair of longitudinally extending and spaced-apart side walls and an end wall joining the outer ends of said side walls and having a strap-receiving opening therethrough;

a row of teeth disposed on one longitudinal surface of said strap and arranged transversely with respect thereto;

a pawl hingedly mounted on and integral with said frame and extending into said strap-receiving opening toward said end wall, said end wall having a strap-bearing surface disposed toward said pawl and said pawl having a strap-engaging surface disposed toward said end wall and defining therewith a strap-receiving channel;

a set of teeth disposed on said strap-engaging surface of said pawl and arranged transversely with respect thereto and shaped complementary to said row of teeth on said strap, said strap being deformable into a loop encircling a bundle of wires with the other end of said strap extending into said strap-receiving channel and through the opening in said frame and therebeyond, said set of teeth being disposed toward said row of teeth as said strap is tightened about living tissue to a tensioned condition, said set of teeth upon release of said tensioned strap sequentially moving into firm engagement with and remaining in firm engagement with successive adjacent ones of said row of teeth, any force tending to withdraw said strap from within said strap-receiving channel in a strap-loosening direction serving to move said set of teeth into more firm engagement with the engaged ones of said row of teeth firmly to wedge said strap between said strap-bearing surface and said strap-engaging surface so as to form said surgical tie into a loop around living tissues and ligate same;

said elongated strap formed of a polymer having a general formula:

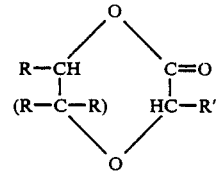

wherein R' and R are individually hydrogen, methyl or ethyl, compressing said tissue utilizing the said surgical tie to the point where normal fluid communication from one said of said surgical tie to the other side of said surgical tie is prevented; and surgically severing one portion of said living tissue adjacent said surgical tie from the other portion thereof.

* * * * *